US00PP23283P2

(12) United States Plant Patent
Miedema-Jorna

(10) Patent No.: US PP23,283 P2
(45) Date of Patent: Dec. 25, 2012

(54) ***PETUNIA* PLANT NAMED 'FIPETROBICO'**

(50) Latin Name: *Petunia×hybrida*
Varietal Denomination: FIPETROBICO

(75) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 36 days.

(21) Appl. No.: 13/134,382

(22) Filed: Jun. 6, 2011

(51) Int. Cl.
*A01H 5/00* (2006.01)

(52) U.S. Cl. ..... Plt./356.21; Plt./356.1

(58) Field of Classification Search ..... Plt./356.1, Plt./356.21
See application file for complete search history.

*Primary Examiner* — Susan McCormick Ewoldt
(74) *Attorney, Agent, or Firm* — C. A. Whealy

(57) ABSTRACT

A new and distinct cultivar of *Petunia* plant named 'Fipetrobico', characterized by its compact, upright to outwardly spreading and mounding growth habit; freely branching habit; freely flowering habit; large light red purple-colored flowers with yellow-colored throats; and good garden performance.

1 Drawing Sheet

Botanical designation: *Petunia×hybrida.*
Cultivar denomination: 'FIPETROBICO'.

BACKGROUND OF THE INVENTION

The present invention relates to a new and distinct *Petunia* plant, botanically known as *Petunia×hybrida* and hereinafter referred to by the name 'Fipetrobico'.

The new *Petunia* plant is a product of a planned breeding program conducted by the Inventor in De Lier, The Netherlands. The objective of the breeding program is to create new freely-branching *Petunia* plants with early and freely flowering habit, and attractive flower color.

The new *Petunia* plant originated from a cross-pollination made by the Inventor in 2007 in De Lier, The Netherlands of a proprietary selection of *Petunia×hybrida* identified as code number For 111060, not patented, as the female, or seed parent with a proprietary selection of *Petunia×hybrida* identified as code number For 111070. The new *Petunia* plant was discovered and selected by the Inventor as a single flowering plant within the progeny of the stated cross-pollination in a controlled greenhouse environment in De Lier, The Netherlands in 2007.

Asexual reproduction of the new *Petunia* plant by terminal cuttings in a controlled greenhouse environment in De Lier, The Netherlands since 2007, has shown that the unique features of this new *Petunia* plant are stable and reproduced true to type in successive generations.

SUMMARY OF THE INVENTION

Plants of the new *Petunia* have not been observed under all possible environmental conditions and cultural conditions. The phenotype may vary somewhat with variations in environment conditions such as temperature and light intensity without, however, any variance in genotype.

The following traits have been repeatedly observed and are determined to be the unique characteristics of 'Fipetrobico'. These characteristics in combination distinguish 'Fipetrobico' as a new and distinct *Petunia* plant:

1. Compact, upright to outwardly spreading and mounding growth habit.
2. Freely branching habit.
3. Freely flowering habit.
4. Large light red purple-colored flowers with yellow-colored throats.
5. Good garden performance.

Plants of the new *Petunia* can be compared to plants of the female parent selection. Plants of the new *Petunia* differ from plants of the female parent selection primarily in flower color as plants of the female parent selection have yellow-colored flowers.

Plants of the new *Petunia* can be compared to plants of the male parent selection. Plants of the new *Petunia* differ from plants of the male parent selection primarily in plant habit as plants of the new *Petunia* are more trailing than and not as upright as plants of the male parent selection.

Plants of the new *Petunia* can be compared to plants of *Petunia×hybrida* 'Famous Pink', not patented. In side-by-side comparisons conducted in De Lier, The Netherlands, plants of the new *Petunia* differed from plants of 'Famous Pink' in the following characteristics:

1. Plants of the new *Petunia* were more compact than plants of 'Famous Pink'.
2. Plants of the new *Petunia* and 'Famous Pink' differed in flower color as flowers of plants of 'Famous Pink' had darker pink-colored flowers.

BRIEF DESCRIPTION OF THE PHOTOGRAPH

The accompanying colored photograph illustrates the overall appearance of the new *Petunia* plant showing the colors as true as it is reasonably possible to obtain in colored reproductions of this type. Colors in the photograph may differ slightly from the color values cited in the detailed botanical description which accurately describe the colors of the new *Petunia* plant. The photograph comprises a side perspective view of a typical flowering plant of 'Fipetrobico' grown in a container.

DETAILED BOTANICAL DESCRIPTION

The aforementioned photograph and following observations, measurements and values describe plants grown in 10.5-cm containers during the spring and early summer in a glass-covered greenhouse in De Lier, The Netherlands. During the production of the plants, day and night temperatures averaging 18° C. Plants were 13 weeks old when the photograph and description were taken. In the following description, color references are made to The Royal Horticultural Society Colour Chart, 2007 Edition, except where general terms of ordinary dictionary significance are used.

Botanical classification: *Petunia×hybrida* 'Fipetrobico'.

Parentage:

*Female, or seed, parent*.—Proprietary selection of *Petunia×hybrida* identified as code number For 111060.

*Male, or pollen, parent*.—Proprietary selection of *Petunia×hybrida* identified as code number For 111070.

Propagation:

*Type*.—By terminal cuttings.

*Time to initiate roots, summer*.—About five to seven days at temperatures of 19° C. to 20° C.

*Time to initiate roots, winter*.—About six to eight days at temperatures of 19° C. to 20° C.

*Time to produce a rooted young plant, summer*.—About 14 to 19 days at temperatures of 19° C. to 20° C.

*Time to produce a rooted young plant, winter*.—About 14 to 21 days at temperatures of 19° C. to 20° C.

*Root description*.—Fine; white in color.

*Rooting habit*.—Freely branching; moderately dense.

Plant description:

*Plant and growth habit*.—Compact, upright to outwardly spreading and mounding growth habit; moderately vigorous growth habit.

*Branching habit*.—Freely branching habit with about six primary lateral branches each with multiple secondary lateral branches; pinching is typically not required.

*Plant height*.—About 18 cm.

*Plant diameter*.—About 35 cm.

Lateral branch description:

*Length*.—About 22 cm.

*Diameter*.—About 4 mm.

*Internode length*.—About 1 cm.

*Strength*.—Moderately strong.

*Aspect*.—Initially upright to outwardly spreading.

*Texture*.—Densely pubescent; viscid.

*Color*.—Close to 144B.

Leaf description:

*Arrangement*.—Alternate, simple; sessile.

*Length*.—About 3.5 cm.

*Width*.—About 2.5 cm.

*Shape*.—Ovate.

*Apex*.—Acute.

*Base*.—Cuneate.

*Margin*.—Entire.

*Texture, upper and lower surfaces*.—Densely pubescent; viscid.

*Venation pattern*.—Pinnate; arcuate.

*Color*.—Developing and fully expanded leaves, upper surface: Close to 137A; venation, close to 137A. Developing and fully expanded leaves, lower surface: Close to 138B; venation, close to 138B.

Flower description:

*Flower arrangement and flowering habit*.—Relatively large salverform flowers arranged singly arising from leaf axils; freely flowering habit with usually about 50 flowers developing per plant; flowers face upright to outwardly.

*Fragrance*.—None detected.

*Natural flowering season*.—Plants typically beginning flowering about 6.5 weeks after planting; plants flower continuously from late spring into the autumn in The Netherlands.

*Flower longevity*.—Individual flowers last about five days on the plant; flowers persistent.

*Flower bud*.—Shape: Narrowly oblanceolate. Length: About 4 cm. Diameter: About 5 mm. Color: Close to 145B.

*Flower diameter*.—About 5.5 cm.

*Flower length (height)*.—About 4 cm.

*Throat diameter*.—About 1 cm.

*Tube length*.—About 3 cm.

*Tube diameter*.—About 3 mm.

*Corolla*.—Arrangement: Five petals fused at the base and opening into a flared trumpet. Petal length from throat: About 2.5 cm. Petal lobe width: About 2.5 cm. Petal shape: Spatulate. Petal apex: Obtuse. Petal margin: Entire. Petal lobe texture, upper and lower surfaces: Smooth, glabrous. Throat texture: Smooth, glabrous. Tube texture: Densely pubescent. Color: Petal, when opening and fully opened, upper surface: Close to 64D; venation, close to 145B; color does not fade with development. Petal, when opening and fully opened, lower surface: Close to 64D; venation, close to 145B. Throat: Close to 1A; venation, close to 145B. Tube: Close to 145B; venation, close to 145B.

*Calyx*.—Arrangement: One star-shaped calyx tube with five sepals per flower, sepals fused at the base. Sepal length: About 1.5 cm. Sepal width: About 4 mm. Sepal shape: Narrowly oblong. Sepal apex: Acute. Sepal base: Cuneate. Sepal margin: Entire. Sepal texture, upper and lower surfaces: Densely pubescent; viscid. Color, upper and lower surfaces: Close to 143A.

*Peduncles*.—Length: About 1.8 cm. Diameter: About 3 mm. Angle: About 40° from stem axis. Strength: Moderately strong. Texture: Densely pubescent; viscid. Color: Close to 144A.

*Reproductive organs*.—Stamens: Quantity per flower: Five. Filament length: About 2 cm. Filament color: Between 155C and 157A. Anther shape: Broadly reniform. Anther length: About 2 mm. Anther color: Close to N155A. Pollen amount: Moderate. Pollen color: Close to 158A. Pistils: Quantity per flower: One. Pistil length: About 2.1 cm. Style length: About 1.7 cm. Style color: Close to 145C. Stigma shape: Flattened, three-lobed. Stigma color: Close to 143A to 143B. Ovary color: Close to 145A. Fruits/seeds: Fruit and seed development have not been observed on plants of the new *Petunia*.

Garden performance: Plants of the new *Petunia* have been observed to have good garden performance and tolerate wind, rain and temperatures ranging from about 5° C. to about 35° C.

Pathogen/pest resistance: Plants of the new *Petunia* have not been observed to be resistant to pathogens and pests common to *Petunia*.

It is claimed:

1. A new and distinct *Petunia* plant named 'Fipetrobico' as illustrated and described.

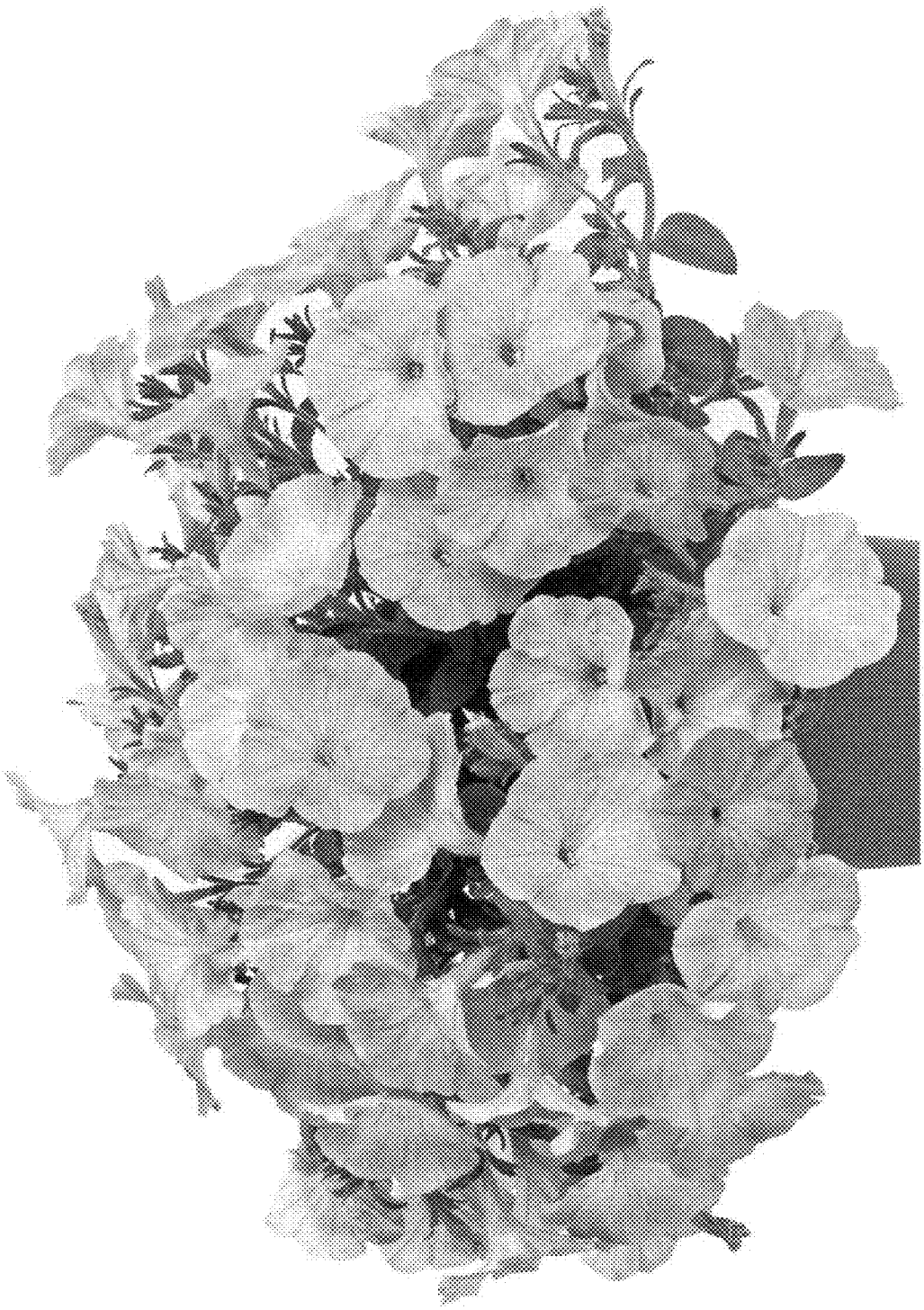

* * * * *